United States Patent [19]

Jacobs et al.

[11] 4,260,560

[45] Apr. 7, 1981

[54] PREPARATION OF SULFAMYL HALIDES

[75] Inventors: Peter Jacobs, Frankenthal; Gerhard Hamprecht, Weinheim; Dietrich Mangold, Neckargemuend, all of Fed. Rep. of Germany

[73] Assignee: BASF Aktiengesellschaft, Fed. Rep. of Germany

[21] Appl. No.: 97,310

[22] Filed: Nov. 26, 1979

[30] Foreign Application Priority Data

Dec. 2, 1978 [DE] Fed. Rep. of Germany ....... 2852274

[51] Int. Cl.$^3$ .............................................. C07C 143/70
[52] U.S. Cl. ............................. 260/543 R; 260/543 F; 560/150
[58] Field of Search ........................ 260/543 R, 543 F

[56] References Cited

U.S. PATENT DOCUMENTS

| | | | |
|---|---|---|---|
| 2,888,486 | 5/1959 | Gregory | 260/543 R |
| 3,621,017 | 11/1971 | Zeidler | 260/243 R |
| 3,822,257 | 7/1974 | Hamprecht | 260/243 R |
| 3,849,467 | 11/1974 | Mangold | 260/456 |
| 3,870,740 | 3/1975 | Fischer | 260/456 A |
| 3,872,167 | 3/1975 | Hamprecht | 260/518 |
| 3,912,489 | 10/1975 | Fischer | 71/91 |
| 3,992,444 | 11/1976 | Hamprecht | 260/543 R |
| 3,997,531 | 12/1976 | Fischer | 260/243 R |
| 4,014,931 | 3/1977 | Hamprecht | 260/543 R |
| 4,096,181 | 6/1978 | Hamprecht | 260/543 R |
| 4,097,521 | 6/1978 | Merkle | 260/543 R |
| 4,101,571 | 7/1978 | Koenig | 560/243 R |
| 4,104,298 | 8/1978 | Koenig | 560/243 R |

FOREIGN PATENT DOCUMENTS 1307726 2/1973 United Kingdom .
1405639 9/1975 United Kingdom .
1496174 12/1977 United Kingdom .

*Primary Examiner*—Natalie Trousof
*Assistant Examiner*—Michael Shippen
*Attorney, Agent, or Firm*—Keil & Witherspoon

[57] ABSTRACT

Sulfamyl halides are prepared by reacting sulfamic acids with halogen in the presence of phosphorus or of a phosphorus trihalide; the sulfamic acid can first be prepared from an isocyanate or urea and then be reacted as above in a one-vessel method.

The compounds obtainable by the process of the invention are valuable starting materials for the preparation of crop protection agents, dyes and drugs.

15 Claims, No Drawings

PREPARATION OF SULFAMYL HALIDES

The present invention relates to a novel process for the preparation of sulfamyl halides by reacting sulfamic acids with halogen in the presence of phosphorus or a phosphorus trihalide; the sulfamic acid can first be prepared from an isocyanate or urea and then be reacted as above in a one-vessel method.

German Laid-Open Application DOS No. 2,164,176 discloses that sulfamyl halides may be prepared by reacting sulfamic acids with an acid halide of sulfurous acid, phosphoric acid, phosphorous acid, carbonic acid or oxalic acid. Thionyl chloride, thionyl bromide, phosphorus pentachloride, phosphorus trichloride, phosphorus oxychloride, phosphorus pentabromide, phosphorus tribromide, phosgene, oxalyl chloride and oxalyl bromide are disclosed as preferred acid halides. As is shown by the Examples, only a single acid halide is used in each case. Apart from phosgene and phosphorus pentachloride, for each of which one example is given, the Examples illustrate only the use of thionyl chloride as the starting halide. The process is unsatisfactory in respect of protection of the environment if thionyl halides are used, and in respect of yield and purity of the end product if the other acid halides, for example phosphorus pentachloride (Example 2b), are used. In carrying out the synthesis using thionyl chloride, not only 1 mole of hydrogen chloride but also 1 mole of sulfur dioxide is always formed per mole of sulfamyl halide; the sulfur dioxide must be taken out of the off-gas by trapping it as bisulfite with sodium hydroxide solution, and the bisulfite must then be concentrated and dumped. Furthermore, the separation of the excess thionyl chloride, used in the reaction, from the chlorohydrocarbons preferentially used as solvents proves difficult, because the differences in boiling point are in most cases slight. If the reaction is carried out with phosphorus trichloride, which is merely mentioned but not used in the Examples, unsatisfactory results are obtained.

German Laid-Open Application DOS No. 2,514,937 describes a further synthesis—which is also more advantageous with respect to protection of the environment—of sulfamyl halides from the corresponding sulfamic acids. In this method, the reaction is carried out using a phosphorus pentahalide as the acid halide, in an amount of from 0.35 to 0.6 mole per mole of starting material, in the presence of from 1 to 5 moles of phosphorus oxyhalide per mole of phosphorus pentahalide, and in the presence of from 50 to 300 percent by weight, based on sulfamic acid, of a halohydrocarbon as the solvent. The said DOS also refers to the possibility, described in U.S. Pat. No. 1,906,440, of first preparing phosphorus pentachloride from phosphorus trichloride or phosphorus in phosphorus oxychloride by treatment with chlorine, but expressly states that this preparation of phosphorus pentachloride must be carried out first, and the sulfamic acids must thereafter be reacted with the resulting suspension of phosphorus pentachloride. Example 4 shows that the suspensions thus obtained contain, prior to addition of the sulfamic acid, the phosphorus pentachloride formed from the starting materials, suspended in phosphorus oxychloride. Furthermore, the process disclosed in U.S. Pat. No. 1,906,440 is expressly stated there to be a method for the preparation of suspensions of finely divided phosphorus pentachloride. The said U.S. Patent shows, in Example 3, concerning a reaction with p-nitrobenzoic acid, that only such a special suspension of phosphorus pentachloride is suitable for subsequent syntheses. A disadvantage of the process of DOS No. 2,514,937 is that it uses phosphorus pentachloride, which is difficult to obtain and uneconomical, or that an additional and troublesome operation to prepare the said chloride is entailed.

We have found that a sulfamyl halide of the formula

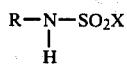

$$R-N-SO_2X \qquad \text{I}$$
$$\phantom{R-N-}H$$

where R is an aliphatic or cycloaliphatic radical and X is halogen may be obtained in an advantageous manner by reacting a sulfamic acid or a metal salt thereof with a halogenating agent in the presence of a solvent, if (a) a sulfamic acid of the formula

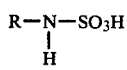

$$R-N-SO_3H \qquad \text{II}$$
$$\phantom{R-N-}H$$

where R has the above meaning, or a metal salt thereof, is reacted with a halogen as the halogenating agent in the presence of phosphorus or a phosphorus trihalide, or (b) in a first stage, an isocyanate of the formula

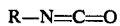

$$R-N=C=O \qquad \text{III}$$

where R has the above meaning, is reacted with sulfuric acid to give a sulfamic acid of the formula

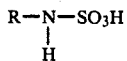

$$R-N-SO_3H \qquad \text{II}$$
$$\phantom{R-N-}H$$

where R has the above meaning, and thereafter, in a second stage, compound II or a metal salt thereof is reacted with a halogen as the halogenating agent, in the presence of phosphorus or a phosphorus trihalide, or (c) a substituted urea of the formula

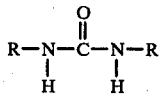

$$R-N-\underset{\underset{H}{|}}{\overset{\overset{O}{\|}}{C}}-N-R \qquad \text{IV}$$
$$\phantom{R-}H \phantom{-C-} H$$

where R has the above meaning, is reacted with oleum, which contains from 1 to 2.5 moles of sulfur trioxide and from 1 to 1.5 moles of sulfuric acid per mole of starting material II, in a first step at from −20° to +50° C. and then in a second step at from 50° C. to 140° C., after which the resulting sulfamic acid of the formula

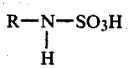

$$R-N-SO_3H \qquad \text{II}$$
$$\phantom{R-N-}H$$

where R has the above meaning, or a metal salt thereof, is reacted, in a third step, with a halogen as the halogenating agent, in the presence of phosphorus or a phosphorus trihalide.

Where ethylsulfamic acid, phosphorus or phosphorus trichloride and chlorine are used, the reaction may be represented by the following equations:

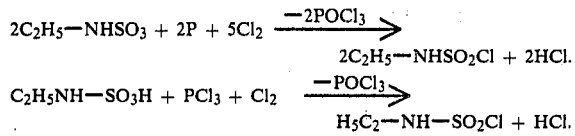

$$2C_2H_5-NHSO_3 + 2P + 5Cl_2 \xrightarrow{-2POCl_3} 2C_2H_5-NHSO_2Cl + 2HCl$$

$$C_2H_5NH-SO_3H + PCl_3 + Cl_2 \xrightarrow{-POCl_3} H_5C_2-NH-SO_2Cl + HCl$$

Compared to the conventional process using sulfur-free halides, the process according to the invention gives sulfamyl halides more simply and more economically, in good yield and high purity. Compared to reactions with thionyl halides, the yield and purity are as good or better, but the essential advantage of the process according to the invention is that working up is easier, there are fewer difficulties in dealing with the off-gas and effluent, and hence there is improved protection of the environment. The separate preparation of an acid halide, and the additional use of large amounts of phosphorus oxychloride, are avoided, hence resulting in savings in respect of plant and instrumentation. Since, from the point of view of operating safety, toxicity of the components, measures for protecting the operators, and problems with effluent and off-gas, large quantities of phosphorus pentachloride suspensions can be handled industrially only if special measures are taken, the process according to the invention is simpler, more economical, safer and less detrimental to the environment. All these advantageous results of the process according to the invention are surprising in view of the prior art. In particular, direct attack of halogen on the starting material and reduced formation of phosphorus halide, and hence blockage of the reaction or substantially reduced formation of sulfamyl halide, would have been expected. For example, it is known from Houben-Weyl, Methoden der Organischen Chemie, Volume 5/3, pages 796–798, and Ullmanns Encyklopädie der technischen Chemie (3rd edition), Volume 5, pages 384 and 385, that ammonia, primary and secondary amines, and carbamic acid esters react with chlorine to give the corresponding N-monochloro or N,N-dichloro compounds; the reaction takes place under alkaline or non-alkaline conditions. Equally, German Published Application DAS No. 1,001,254 shows the chlorination of nitrogen compounds, eg. biguanide derivatives, in acid solution.

Preferred starting materials II, III and IV and accordingly preferred end products I are those where R is straight-chain or branched alkyl of 1 to 20, especially of 1 to 8, carbon atoms, or alkyl of 2 to 20, especially of 2 to 8, advantageously of 2 to 6, carbon atoms which is substituted by several alkoxy groups, preferably 3 or 2 alkoxy groups, and in particular by one alkoxy group of 1 to 7, especially of 1 to 3, carbon atoms, or is cycloalkyl of 4 to 8 carbon atoms, and X is bromine or especially chlorine. The above radicals may in addition be substituted by groups and/or atoms which are inert under the reaction conditions, eg. chlorine, bromine, alkyl or alkoxy each of 1 to 4 carbon atoms, carbalkoxy of 2 to 4 carbon atoms or cycloalkyl of 4 to 6 carbon atoms.

Examples of suitable sulfamic acids II are methylsulfamic acid, ethylsulfamic acid, n-propylsulfamic acid, isopropylsulfamic acid, n-butylsulfamic acid, isobutylsulfamic acid, sec.-butylsulfamic acid, cyclobutylsulfamic acid, 1-ethyl-1-propylsulfamic acid, 1,2-dimethyl-1-propylsulfamic acid, n-pentylsulfamic acid, cyclopentylsulfamic acid, n-hexylsulfamic acid, hex-3-yl-sulfamic acid, cyclohexylsulfamic acid, cycloheptylsulfamic acid, hept-4-yl-sulfamic acid, cyclooctylsulfamic acid, 2-methyl-1-ethyl-propyl-1-sulfamic acid, 1,2,2-trimethyl-propyl-1-sulfamic acid, 1,3-dimethyl-n-butyl-1-sulfamic acid, 1,2-dimethyl-n-butyl-1-sulfamic acid, 1,2-dimethyl-n-hexyl-1-sulfamic acid, 1-cyclohexylethyl-1-sulfamic acid, 2-chloro-isopropylsulfamic acid, 2-chloropropylsulfamic acid, 3-chloropropylsulfamic acid, 3-bromopropylsulfamic acid and 1-chloromethyl-propyl-1-sulfamic acid; tert.-butyl-, pent-2-yl-, n-heptyl-, n-octyl-, n-nonyl-, n-decyl-, 2-ethylhexyl-, 2-ethyl-pentyl-, 3-ethylpentyl-, 2,3-dimethyl-n-butyl-, 2-methylpentyl-, 3-methylpentyl-, 2-methylheptyl-, 3-methylheptyl-, 4-methylheptyl-, 3-ethylhexyl-, 2,3-dimethylhexyl-, 2,4-dimethylhexyl-, 2,5-dimethylhexyl-, undecyl-, dodecyl-, tridecyl-, tetradecyl-, pentadecyl-, hexadecyl-, heptadecyl-, octadecyl-, nonadecyl- and eicosyl-sulfamic acid; the ω-methoxy-, ω-ethoxy-, ω-n-propoxy-, ω-isopropoxy-, ω-n-butoxy-, ω-isobutoxy-, ω-sec.-butoxy-, ω-tert.-butoxy-, ω-pentoxy-, ω-pent-2-oxy-, ω-pent-3-oxy-, ω-n-hexoxy- and ω-n-heptoxy-derivatives of ethyl-, n-propyl-, isopropyl-, n-butyl-, isobutyl-, sec.-butyl-, tert.-butyl-, pentyl-, pent-2-yl-, pent-3-yl-, n-hexyl-, n-heptyl-, n-octyl-, n-nonyl-, n-decyl-, 2-ethylhexyl-, 2-ethylpentyl-, 3-ethylpentyl-, 2,3-dimethyl-n-butyl-, 2-methylpentyl-, 3-methylpentyl-, 2-methylheptyl-, 3-methylheptyl-, 4-methylheptyl-, 3-ethylhexyl-, 2,3-dimethylhexyl-, 2,4-dimethylhexyl-, 2,5-dimethylhexyl-, undecyl-, dodecyl-, tridecyl-, tetradecyl-, pentadecyl-, hexadecyl-, heptadecyl-, octadecyl-, nonadecyl- and eicosyl-sulfamic acid; and the corresponding methyl-, ethyl-, n-propyl-, isopropyl-, n-butyl-, isobutyl-, sec.-butyl-, tert.-butyl-, pentyl-, pent-2-yl-, pent-3-yl-, n-hexyl- and n-heptyl-ethers with the ether group in the 1-position or 2-position of the n-propyl-, isopropyl-, n-butyl-, isobutyl-, sec.-butyl-, tert.-butyl-, pentyl-, pent-2-yl-, pent-3-yl-, n-hexyl-, n-heptyl-, n-octyl-, n-nonyl-, n-decyl-, 2-ethylhexyl-, 2-ethylpentyl-, 3-ethylpentyl-, 2,3-dimethyl-n-butyl-, 2-methylpentyl-, 3-methylpentyl-, 2-methylheptyl-, 3-methylheptyl-, 4-methylheptyl-, 3-ethylhexyl-, 2,3-dimethylhexyl-, 2,4-dimethylhexyl-, 2,5-dimethylhexyl-, undecyl-, dodecyl-, tridecyl-, tetradecyl-, pentadecyl-, hexadecyl-, octadecyl-, nonadecyl- and eicosyl-sulfamic acid, or in the 1-position of ethylsulfamic acid.

The starting materials II may be used in the form of sulfamic acids, for example the sulfamic acids, free from sulfuric acid, prepared by the processes described in German Laid-Open Applications DOS Nos. 2,424,371 and 2,164,197, or in the form of their metal salts. Preferred metal salts are those of the alkali metals or alkaline earth metals, eg. magnesium, calcium, lithium, potassium and especially sodium. The phosphorus used may be black, red or, preferably, yellow phosphorus. The preferred halogens are bromine and especially chlorine and the preferred phosphorus trihalides are phosphorus tribromide and especially phosphorus trichloride. The halogen, phosphorus and/or phosphorus trihalide may be employed in stoichiometric amount or in excess for the reaction with the starting material II, advantageously in an amount of from 1 to 1.5, preferably from 1 to 1.2, moles of phosphorus trihalide or gram atoms of phosphorus per mole of starting material II, and/or advantageously in an amount of from 1 to 1.5, especially from 1 to 1.2, moles of halogen, where phosphorus trihalide is used, or advantageously from 2.5 to 3.3, especially from 2.5 to 3, moles of halogen where phosphorus is used, the said amounts being per mole of starting material II.

The reaction is as a rule carried out at from $-10°$ to 130° C., preferably from 10° to 120° C., especially from 40° to 100° C., under atmospheric or superatmospheric pressure, continuously or batchwise. Organic solvents which are inert under the reaction conditions are used, and in the case of procedures (b) and (c) it is advantageous to add the total amount of organic solvent when carrying out the first reaction step. Examples of suitable solvents are halohydrocarbons, advantageously non-aromatic halohydrocarbons, especially chlorohydrocarbons, eg. tetrachloroethylene, amyl chloride, cyclohexyl chloride, dichloropropane, methylene chloride, dichlorobutane, carbon tetrachloride, tetrachloroethane, trichloroethane, trichloroethylene, pentachloroethane, trichlorofluoromethane, cis-dichloroethylene, 1,2-dichloroethane, 1,1-dichloroethane, n-propyl chloride, 1,2-cis-dichloroethylene, n-butyl chloride, 2-, 3- and isobutyl chloride and mixtures of these. The solvent is advantageously used in an amount of from 50 to 10,000 percent by weight, preferably from 300 to 1,000 percent by weight, based on starting material II or III or IV.

For procedure (a), the reaction may be carried out as follows: A mixture of starting material II, phosphorus or phosphorus trihalide and solvent is kept at the reaction temperature for from 0.5 to 8 hours, whilst passing the appropriate halogen into the mixture. The end product I is isolated from the reaction mixture in the conventional manner, for example after distilling off the solvent and the phosphorus oxyhalide formed as a by-product.

In the advantageous embodiment (b), the reaction mixture from the preparation of the starting material II is used, without isolating II, as the starting mixture for the process according to the invention, with or without first adding a solvent. Preferably, the reaction mixture described in German Laid-Open Application DOS No. 2,164,197 is used as the starting mixture. This is obtained on reacting an isocyanate with anhydrous sulfuric acid at not less than 25° C. in an inert solvent, for example one of the above halohydrocarbons. The following procedure is preferred: A mixture of starting material III and solvent, and sulfuric acid or a mixture of sulfuric acid and solvent, are introduced simultaneously but separately, with vigorous stirring, into a receiver containing solvent. The addition is advantageously made over from 10 to 55 minutes, commonly at from 25° to 50° C., after which the reaction is carried out at not less than 50° C., advantageously from 50° to 120° C. Advantageously, the solvent chosen is the same as the halohydrocarbon used for the process according to the invention. Advantageously, phosphorus or phosphorus trihalide is added at this stage, with or without a further quantity of solvent, and the reaction according to the invention is then carried out, as a second step, for from 0.5 to 8 hours, with introduction of halogen. If appropriate, the reaction temperature is varied within the above temperature range, for example it is raised from 60° to 120° C., in particular from 60° to 80° C. The end product I is isolated in the manner described above.

Advantageous starting materials III to use for procedure (b) are the isocyanates mentioned above, which are homologous with the sulfamic acids II mentioned by way of example or mentioned as being preferred. The solvents used are advantageously those mentioned above for procedure (a). In other respects, namely as regards the reaction temperature, pressure, continuous or batchwise operation, solvents, amounts of solvents, sulfuric acid, oleum, ratios of the reactants, reaction conditions for the first step of (b) and reaction time, the reaction is carried out in accordance with German Laid-Open Application DOS No. 2,164,197, especially pages 3 to 5.

Procedure (c) is more advantageous than procedure (b), and the latter is more advantageous than procedure (a). Surprisingly, in view of the prior art, procedure (c) offers particularly advantageous results. The advantageous starting materials IV are the substituted ureas which are analogous to the sulfamic acids II mentioned above as being preferred, or by way of example. Where N,N'-dimethylurea is used, the reaction occurring in the first and second steps of procedure (c) can be represented by the following equation:

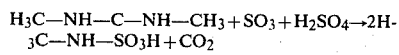

The following ureas are particularly suitable starting materials IV: N,N'-dimethylurea, N,N'-diisopropylurea, N,N'-di-n-butylurea, N,N'-didodecylurea, N,N'-di-sec.-butylurea, N,N'-di-tert.-butylurea, N,N'-diethylurea, N,N'-dicyclohexylurea and N,N'-di-n-propylurea.

The reaction, even in the first step of procedure (c), and hence in the entire reaction, comprising the first and second steps is carried out with from 1 to 2.5, preferably from 1 to 1.5, especially from 1 to 1.1, moles of sulfur trioxide and with from 1 to 1.5, preferably from 1 to 1.2, especially from 1 to 1.1, moles of sulfuric acid per mole of starting material IV. The preferred ratio is about 1 mole of sulfur trioxide per mole of $H_2SO_4$, and the deviations from the stoichiometric ratio are advantageously less than 10 percent by weight. The use of 45 percent strength by weight oleum (pyrosulfuric acid, $H_2S_2O_7$) in the above ratios, especially of 178–195 percent by weight of oleum, based on the weight of one mole of starting material IV, is particularly preferred. Instead of oleum, which is advantageously 45 percent strength by weight oleum, it is also possible to use mixtures of more concentrated oleum and/or sulfur trioxide with less concentrated oleum, sulfuric acid and/or water, the mixture being adjusted to be equivalent to an oleum containing the amounts of sulfur trioxide and amounts of sulfuric acid required according to the invention. The sulfuric acid used to prepare the oleum is as a rule employed in the form of 100% strength sulfuric acid (ie. sulfur trioxide monohydrate). If desired, aqueous sulfuric acid of from 96 to just under 100 percent strength by weight can also be used to prepare the oleum. Sulfur trioxide can be employed in the solid or, advantageously, in the liquid form, or as a gas, for preparing the oleum; advantageously, 100 percent strength sulfur trioxide is used to prepare the oleum, though the sulfur trioxide can also be diluted with an inert gas such as carbon dioxide or nitrogen. However, it is also possible to prepare the oleum using compounds which liberate sulfur trioxide under the conditions of mixing employed, for example adducts of sulfur trioxide, for instance with ethers, eg. tetrahydrofuran, di-(β-chloroethyl) ether or 1,4-dioxane, with N,N-di-substituted carboxylic acid amides, eg. N,N-dimethylformamide, or with tertiary amines, eg. pyridine, triethylamine, trimethylamine, tributylamine, quinoline, quinaldine, dimethylaniline, triphenylamine, N-methylmorpholine, N-ethylmorpholine, N-methylpiperidine, N-ethylimidazole, N-methylethyleneimine or N-ethylpentamethyleneimine, or adducts of chlorosulfonic acid with the above amines, especially with pyridine, or mixtures of the above adducts. As regards the definition of 100 percent strength sulfur trioxide, reference may be made to Ullmanns Encyklopte,um/a/ die der technischen Chemie, Volume 15, pages 465–467, and as regards the preparation of adducts, reference may be made to Houben-Weyl (loc. cit.), Volume VI/2, pages 455–457, and Volume IX, pages 503–508.

In the first step of procedure (c), the reaction is carried out at from −20° C. to +50° C., advantageously from −10° C. to +30° C., preferably from −5° C. to +27° C., whilst in the second step it is carried out at from above 50° C. to below 140° C., advantageously from 51° C. to 100° C., preferably from 51° C. to 85° C., under atmospheric or superatmospheric pressure, continuously or batchwise. Organic solvents which are inert under the reaction conditions are used, and advantageously the total amount of organic solvent is added even for the first reaction step. Examples of suitable solvents are those mentioned above, especially halohydrocarbons.

The reaction may be carried out as follows: A mixture of starting material IV, solvent and oleum is kept for from 0.2 to 2 hours at the reaction temperature of the first step. Advantageously, the urea IV is first suspended in a solvent and the oleum is introduced into the mixture, with thorough mixing. In the second reaction step, the mixture is then kept at the reaction temperature used for the second step for from 0.2 to 5 hours. Thereafter, phosphorus or phosphorus trihalide is advantageously added, with or without a further quantity of solvent, and halogen is introduced whilst carrying out the reaction according to the invention in the third step for from 0.5 to 8 hours. If appropriate, the reaction temperature is additionally varied within the temperature range stated above, for example raised from 60° to 130° C., especially from 60° to 100° C. The end product I is isolated in the manner described above.

The compounds obtainable by the process of the invention are valuable starting materials for the preparation of crop protection agents, dyes and drugs. For example, the o-sulfamidobenzoic acids described in German Laid-Open Application DOS No. 2,104,682 may be prepared from the compounds by reaction with anthranilic acid or a salt thereof. Cyclization of the said o-sulfamidobenzoic acids, for example by the process described in German Laid-Open Application DOS No. 2,105,687, gives the 2,1,3-benzothiadiazin-4-one-2,2-dioxides, the use of which as crop protection agents and drugs is described in the same patent application. The very good herbicidal properties of this category of compounds are described in U.S. Pat. No. 3,621,017, German Pat. No. 1,937,551 and German Laid-Open Application DOS No. 2,131,401.

The use of the compounds as important intermediates for herbicides is also to be found in German Pat. No. 1,542,836 and German Laid-Open Application DOS No. 2,349,114. Furthermore, reaction of alkylsulfamyl chlorides with sulfenyl chlorides by the process of German Pat. No. 1,953,356 results in fungicide intermediates.

Reaction of the end products I with substituted glycolic acid anilides gives yet other herbicides (German Laid-Open Applications DOS No. 2,201,432 and DOS No. 1,310,757).

Finally, the 2,1,3-benzothiadiazin-4-one-2,2-dioxides obtainable from N-alkylsulfamyl chlorides exhibit valuable pharmacological properties. U.S. Pat. No. 3,041,336 states that 3-oxo-1,2,6-thiadiazine-1,1-dioxides are used in practice as antiphlogistics, antipyretics and analgesics.

In the Examples which follow, parts are by weight and bear the same relation to parts by volume as that of the kilogram to the liter.

EXAMPLE 1

(A) 58 parts of N,N'-diethylurea are suspended in 290 parts by volume of 1,2-dichloroethane. 89 parts of oleum (containing 45 percent by weight of $SO_3$) are added to the mixture at 20°–25° C. The mixture is then heated to 75° C. and kept at this temperature for two hours.

(B) The mixture is then cooled. 137.5 parts of phosphorus trichloride are added at 50° C. and chlorine (77 parts) is passed into the mixture for two hours at 50°–75° C., until chlorine becomes detectable in the off-gas. Small amounts of solid are filtered off and the filtrate is then freed from solvent and phosphorus oxychloride under reduced pressure.

Yield: 124 parts of ethylsulfamyl chloride (86.7% of theory), of boiling point 67° C./0.01 mbar.

EXAMPLE 2

(A) 44 parts of N,N'-dimethylurea are suspended in 300 parts by volume of 1,2-dichloroethane. 89 parts of oleum (containing 45 percent by weight of $SO_3$) are added to the mixture at 20°–25° C. The mixture is then heated to 75° C. and kept at this temperature for two hours. The mixture is then cooled.

(B) 137.5 parts of phosphorus trichloride are added at 50° C. and chlorine (77 parts) is passed into the mixture for two hours at 50°–75° C., until chlorine becomes detectable in the off-gas. Small amounts of solid are filtered off and the filtrate is then freed from solvent and phosphorus oxychloride under reduced pressure.

Yield: 110 parts of methylsulfamyl chloride (85.2% of theory), of boiling point 74°–77° C./0.2 mbar.

EXAMPLE 3

Ethylamidosulfonic acid is prepared analogously to Example 1 A). Thereafter 31 parts of yellow phosphorus are added to the resulting suspension in 1,2-dichloroethane at 50° C., and chlorine (195 parts) if passed into the mixture for two hours at 50°–75° C., until it becomes detectable in the off-gas. The solvent and phosphorus oxychloride are then stripped off under reduced pressure.

Yield: 127.5 parts of ethylsulfamyl chloride (88.8% of theory) of boiling point 67° C./0.01 mbar.

EXAMPLE 4

Methylamidosulfonic acid is prepared analogously to Example 2(A). Thereafter 31 parts of yellow phosphorus are added to the resulting suspension in 1,2-dichloroethane at 50° C., and chlorine (195 parts) is passed into the mixture for two hours at 50°–75° C., until it becomes detectable in the off-gas. Small amounts of solid are filtered off and the filtrate is then freed from solvent and phosphorus oxychloride under reduced pressure.

Yield: 101 parts of methylsulfamyl chloride (78.1% of theory) of boiling point 74°–77° C./0.2 mbar.

EXAMPLE 5

222 parts of methylamidosulfonic acid are suspended in 800 parts by volume of 1,2-dichloroethane. 275 parts of phosphorus trichloride are added to the mixture at 25° C. and chlorine (145 parts) is passed in for two hours at 65° C., until it becomes detectable in the off-gas. Small amounts of solid are filtered off and the filtrate is then freed from solvent and phosphorus oxychloride under reduced pressure.

Yield: 212.5 parts of methylsulfamyl chloride (82% of theory) of boiling point 74°–77° C./0.2 mbar.

EXAMPLE 6

125 parts of ethylamidosulfonic acid are suspended in 750 parts by volume of 1,2-dichloroethane. 31 parts of yellow phosphorus are added to the mixture at 50° C. and chlorine (195 parts) is passed in for two hours at 60° C., until it becomes detectable in the off-gas. Small amounts of solid are filtered off and the filtrate is then freed from solvent and phosphorus oxychloride under reduced pressure.

Yield: 118 parts of ethylsulfamyl chloride (82.3% of theory) of boiling point 67° C./0.01 mbar.

EXAMPLE 7

44 parts of isopropylamidosulfonic acid are suspended in 750 parts by volume of 1,2-dichloroethane. 10 parts of yellow phosphorus are added to the mixture at 50° C. and chlorine (60 parts) is passed in for two hours at 50°–75° C., until it becomes detectable in the off-gas. Small amounts of solid are filtered off and the filtrate is then freed from solvent and phosphorus oxychloride under reduced pressure.

Yield: 37.9 parts of isopropylsulfamyl chloride (76% of theory) of boiling point 78°–83° C./0.2 mbar.

EXAMPLE 8

(A) 71 parts of ethyl isocyanate in 50 parts by volume of 1,2-dichloroethane are added, in the course of 20 minutes, with vigorous stirring, to a mixture of 100 parts of oleum (containing 2 percent by weight of $SO_3$) and 320 parts by volume of 1,2-dichloroethane at 25°–27° C. The mixture is then kept for 20 minutes at 75° C., until the evolution of carbon dioxide has ceased. Thereafter, it is cooled.

(B) 31 parts of yellow phosphorus are then added, at 50° C., to the suspension obtained, and chlorine (195 parts) is passed in for two hours at 50°–75° C., until it becomes detectable in the off-gas. Solvent and phosphorus oxychloride are then stripped off under reduced pressure.

Yield: 126.3 parts of ethylsulfamyl chloride (88% of theory) of boiling point 67° C./0.01 mbar.

EXAMPLE 9

133 parts of the sodium salt of methylamidosulfonic acid are suspended in 750 parts by volume of 1,2-dichloroethane. 31 parts of yellow phosphorus are added at 50° C. and chlorine (195 parts) is passed into the mixture for two hours at 50°–75° C., until it becomes detectable in the off-gas. The mixture is filtered and the filter residue is washed with 1,2-dichloroethane. The filtrate is freed from solvent and phosphorus oxychloride under reduced pressure.

Yield: 104 parts of methylsulfamyl chloride (80.3% of theory) of boiling point 74–77° C./0.2 mbar.

We claim:

1. A process for the preparation of a sulfamyl halide of the formula

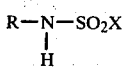

where R is an aliphatic or cycloaliphatic radical and X is halogen, which comprises: reacting a substituted urea of the formula

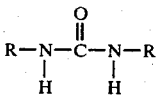

where R has the above meaning, with oleum, which contains from 1 to 2.5 moles of sulfur trioxide and from 1 to 1.5 moles of sulfuric acid per mole of starting material II, in a first step at from −20° to +50° C. and then in a second step at from 50° C. to 140° C., after which the resulting sulfamic acid of the formula

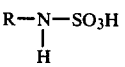

where R has the above meaning, or a metal salt thereof, is reacted, in a third step, with a halogen as the halogenating agent, in the presence of phosphorus or a phosphorus trihalide.

2. A process for the preparation of a sulfamyl halide of the formula

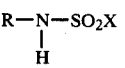

where R is an aliphatic or cycloaliphatic radical and X is halogen, which comprises: reacting a sulfamic acid of the formula

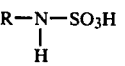

where R has the above meaning, or a metal salt thereof, with a halogen as the halogenating agent, in the presence of phosphorus or a phosphorus trihalide.

3. A process for the preparation of a sulfamyl halide of the formula

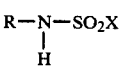

where R is an aliphatic or cycloaliphatic radical and X is halogen, which comprises: reacting in a first stage, an isocyanate of the formula

where R has the above meaning, with sulfuric acid to give a sulfamic acid of the formula

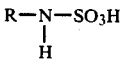

where R has the above meaning, and thereafter, in a second stage, compound II or a metal salt thereof is reacted with a halogen as the halogenating agent, in the presence of phosphorus or a phosphorus trihalide.

4. A process as claimed in claim 1, 2 or 3, wherein the reaction is carried out with bromine or chlorine and phosphorus tribromide or phosphorus trichloride.

5. A process as claimed in claim 1, 2 or 3, wherein the reaction is carried out with from 1 to 1.5 moles of phosphorus trihalide or gram atoms of phosphorus per mole of material II.

6. A process as claimed in claim 1, 2 or 3, wherein the reaction is carried out, when using $PCl_3$, with from 1 to 1.5 moles of halogen, and when using phosphorus, with from 2.5 to 3.3 moles of halogen, per mole of starting material II.

7. A process as claimed in claim 1, 2 or 3, wherein the reaction is carried out at from $-10°$ to $+130°$ C.

8. A process as claimed in claim 1, 2 or 3, wherein the reaction is carried out at from $+10°$ to $120°$ C.

9. A process as claimed in claim 1, 2 or 3, wherein the reaction is carried out at from $40°$ to $100°$ C.

10. A process as claimed in claim 1, 2 or 3, wherein the reaction is carried out in the presence of from 50 to 10,000 percent by weight, based on starting material II or III or IV, of an organic solvent which is inert under the reaction conditions.

11. A process as claimed in claim 3, wherein the reaction, in the first stage, is carried out at not less than $50°$ C.

12. A process as claimed in claim 1, wherein the reaction in the first step is carried out with from 1 to 1.5 moles of sulfur trioxide per mole of starting material IV.

13. A process as claimed in claim 1, wherein the reaction in the first step is carried out with from 1 to 1.2 moles of sulfuric acid per mole of starting material IV.

14. A process as claimed in claim 1, wherein the reaction in the first step is carried out with 45 percent strength by weight oleum (pyrosulfuric acid, $H_2S_2O_7$).

15. A process as claimed in claim 1, wherein the reaction in the first step is carried out at from $-10°$ C. to $+30°$ C., while the second step is carried out at from $51°$ C. to $100°$ C.

* * * * *